(12) United States Patent
Seguin

(10) Patent No.: US 6,830,584 B1
(45) Date of Patent: Dec. 14, 2004

(54) DEVICE FOR REPLACING A CARDIAC VALVE BY PERCUTANEOUS ROUTE

(75) Inventor: Jacques Seguin, 18 rue Montalivet, F-75008 Paris (FR)

(73) Assignee: Jacques Seguin, Paris (FR)

( * ) Notice: Subject to any disclaimer, the term of this patent is extended or adjusted under 35 U.S.C. 154(b) by 112 days.

(21) Appl. No.: 10/130,355

(22) PCT Filed: Nov. 15, 2000

(86) PCT No.: PCT/FR00/03176

§ 371 (c)(1), (2), (4) Date: Nov. 26, 2002

(87) PCT Pub. No.: WO01/35870

PCT Pub. Date: May 25, 2001

(30) Foreign Application Priority Data

Nov. 17, 1999 (FR) .............................. 99 14462

(51) Int. Cl.[7] .................................................. A61F 2/06
(52) U.S. Cl. ..................................................... 623/2.11
(58) Field of Search .............................. 623/2.11, 3.15; 128/898; 606/150, 153, 151

(56) References Cited

U.S. PATENT DOCUMENTS

| 5,156,610 A | | 10/1992 | Reger |
| 5,370,647 A | | 12/1994 | Graber et al. |
| 5,370,685 A | * | 12/1994 | Stevens ...................... 623/2.11 |
| 5,924,424 A | | 7/1999 | Stevens et al. |
| 5,968,064 A | | 10/1999 | Selmon et al. |
| 5,984,959 A | * | 11/1999 | Robertson et al. ......... 623/2.11 |
| 6,413,274 B1 | * | 7/2002 | Pedros ....................... 623/2.11 |
| 6,425,902 B1 | * | 7/2002 | Love ........................... 606/150 |
| 6,451,054 B1 | * | 9/2002 | Stevens ...................... 623/2.11 |
| 2003/0144732 A1 | * | 7/2003 | Cosgrove et al. .......... 623/2.11 |

FOREIGN PATENT DOCUMENTS

| WO | WO 99/12483 | 3/1999 |
| WO | WO 99/15227 | 4/1999 |

* cited by examiner

*Primary Examiner*—Suzette J. Jackson
(74) *Attorney, Agent, or Firm*—Young & Thompson

(57) ABSTRACT

A device for replacing a cardiac valve includes an elongated support element (2), two series of elongated blades (30) arranged around the circumference of the elongated elements (2), where the blades (30) have opposite cutting edges (30a, 30b) and can be extended corolla-shaped such that their cutting edges are set in the extension of one another thereby forming circular cutting edges. The blades (30) can be brought closer together so that their circular cutting edges are urged to cut the native valve (55, 56) so as to separate it from the corporeal duct (50).

11 Claims, 4 Drawing Sheets

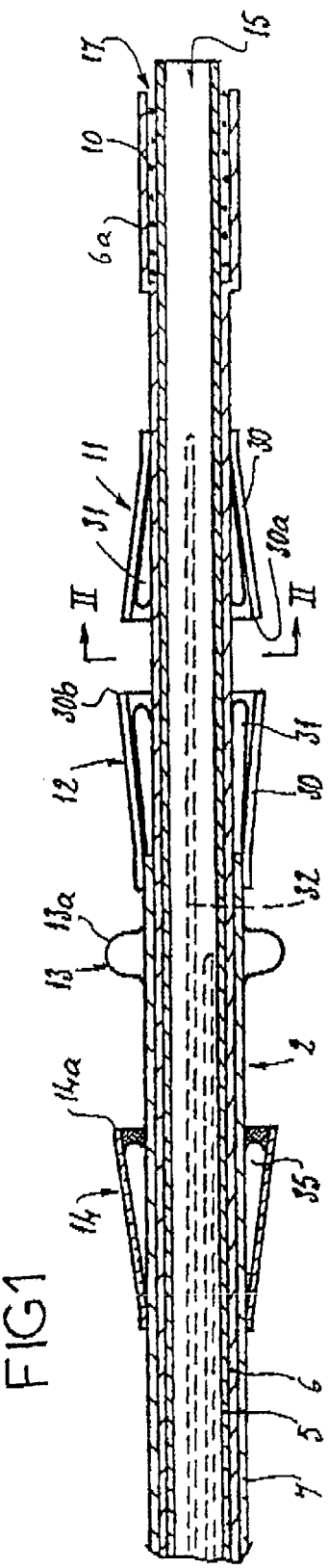
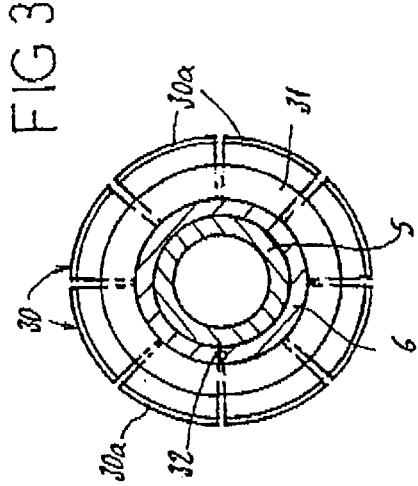
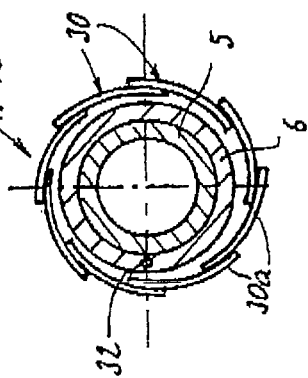

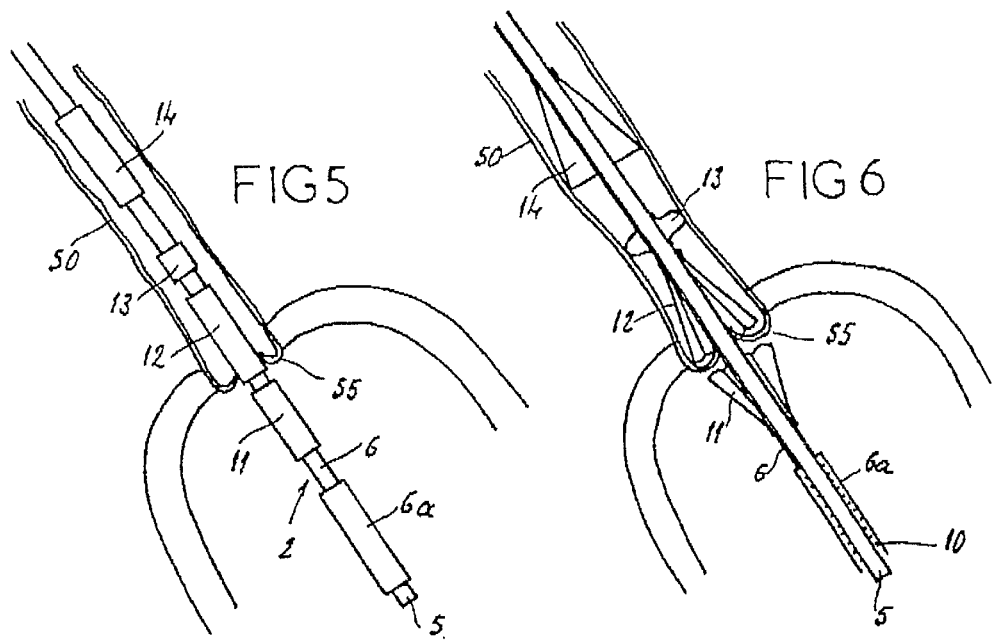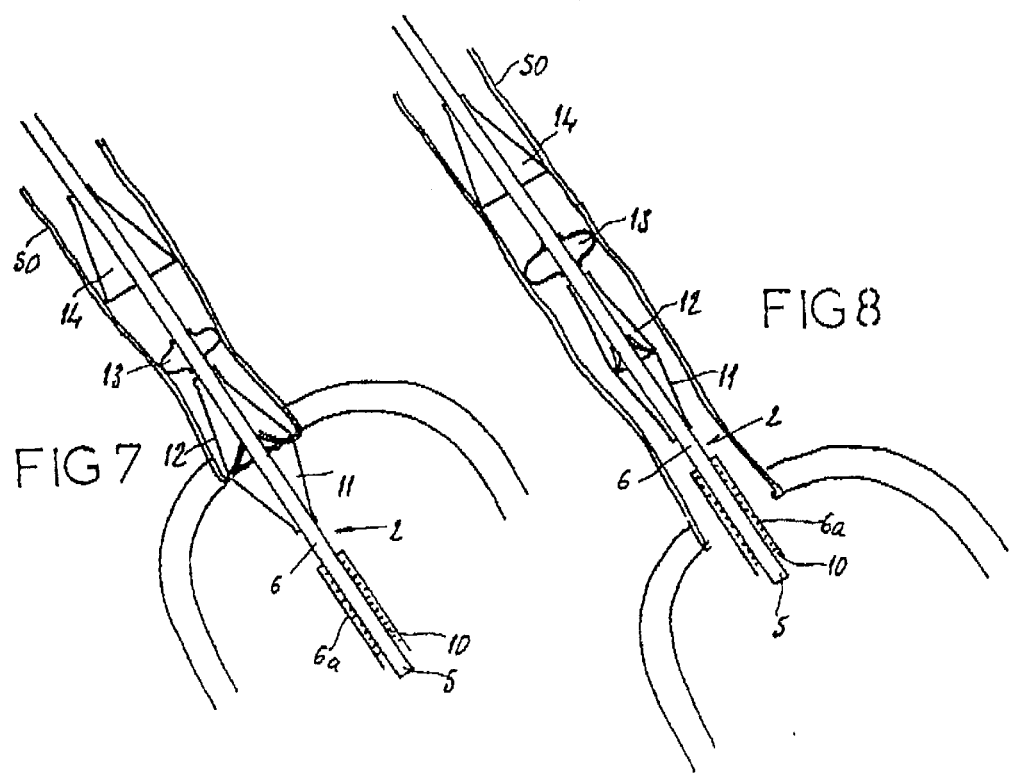

DEVICE FOR REPLACING A CARDIAC VALVE BY PERCUTANEOUS ROUTE

The present invention relates to a device for replacing a heart valve by a percutaneous route.

Replacing a defective heart valve is currently usually performed by opening up the thorax, placing the patient under extra-corporal circulation, temporarily stopping the heart, and opening up the heart so as to cut away and replace the valve.

These successive steps in the operation have the disadvantage of entailing hospitalizing the patient for a relatively long period of time and of being complicated and expensive.

To overcome this drawback it has been envisaged for a heart valve to be replaced by a route which is not so invasive. International (PCT) applications Ser. Nos. WO 93/01768 and WO 97/28807, and U.S. Pat. Nos. 5,814,097, 5,370,685 and 5,545,214 illustrate some known fairly non-invasive techniques and instruments for performing these techniques.

The existing techniques are, however, considered not to be perfectly satisfactory and to be open to improvement. In particular, these techniques have the disadvantage of always involving placing the patient under extra-corporal circulation and temporarily stopping the heart; they are difficult to put into practice; they do not allow precise control over the diameter at which the native valve is cut with a view to subsequently calibrating the prosthetic valve; they run the risk that fragments of, often calcified, native valve will become dispersed into the organism, which may lead to an embolism, and the risks of perforating the wall of the aorta or the heart; they also introduce the risks of acute reflux of blood during ablation of the native valve.

The device according to the present invention has been designed with a view to alleviating the deficiencies of these techniques.

In particular, the object of the invention is to provide a device which is satisfactory as regards the cutting-away and replacement of the valve, by making it possible to perform the intervention without opening up the thorax, stopping the heart and/or opening up the heart, and by making it possible to prevent any dispersion of fragments of the removed valve into the circulatory system.

The terms "distal" and "proximal" used hereinbelow to explain the invention are defined with respect to the direction in which the blood flows.

The device according to the invention comprises:

an elongate support element;

a first series of elongate blades arranged around the circumference of said elongate element; these blades are pivotably connected to the elongate element at their proximal longitudinal end and each have a cutting edge at their distal longitudinal end; these blades can pivot with respect to the elongate element between a furled position in which they are near to the wall of the elongate element so that they do not impede the introduction and sliding of the device into and in the bodily vessel in which the valve is located, particularly within the aorta, and an unfurled position in which these blades are deployed into a corolla in such a way that their cutting edges are placed in the continuation of one another and thus constitute a circular cutting edge;

a second series of blades which is arranged after said first series of blades in the distal direction; the blades of this second series of blades have a structure identical to that of the blades of said first series of blades except that these blades of this second series are connected to the elongate element by their distal longitudinal end and each have a cutting edge at their proximal longitudinal end;

means for bringing the blades of said first and second series of blades from their furled position to their unfurled position;

means for moving said series of blades axially toward one another, between a position in which these series of blades are away from each other and in which one series of blades can be placed axially on one side of the native valve while the other series of blades is placed axially on the other side of this valve, and a close-together position in which the circular cutting edges of these two series of blades are brought into mutual contact and thus cut through the native valve so as to detach it from said bodily vessel; and means of identifying, by a percutaneous route, the axial position of the device with respect to the native valve so as to position each of the two aforementioned series of blades on one side of this valve.

The device according to the invention may be introduced percutaneously into said bodily vessel and slid along this vessel until each of the aforementioned series of blades is placed on one side of the valve. This position is identified using said identifying means.

A peripheral profusion or extra corporal circulation system may be set in place to facilitate the flow of the blood, with a view to preventing blood from pooling in the heart.

After the aforementioned positioning of the device, the blades of the two series of blades are deployed, then these two series are brought closer together until they cut through the valve. The shaping of these blades allows this cutting to be performed in a single operation, therefore without generating fragments likely to be dispersed into the circulatory system, or at the very least generating only very few such fragments; this shaping also allows precise control over the diameter at which the native valve is cut, with a view to subsequent calibration of the prosthetic valve.

The blades are then returned to the furled position.

The prosthetic valve is then put in place.

This valve may be separate from the device, in which case the latter is removed, then the prosthetic valve is introduced and positioned in the said bodily vessel by means of a separate device. As a preference, however, the device according to the invention comprises a proximal prosthetic valve, with a radially deployable structure, it being possible for this prosthetic valve to occupy a furled position in which it is near the wall of said elongate element and does not impede the introduction and sliding of the device into and in said bodily vessel, and an unfurled position in which it bears against the wall of this vessel and is able to replace the native heart valve.

The device thus allows the prosthetic valve to be introduced and positioned at the appropriate point in the bodily vessel, through the same action as the one which allowed the native valve to be cut out. After the latter has been cut out, the device is slid axially in the distal direction so as to position the prosthetic valve at the appropriate point in this vessel, after which this prosthetic valve is deployed. The device is then withdrawn and the cut-out native valve is recovered.

As a preference, said elongate support element is a tubular catheter.

This catheter thus allows the blood to flow through it during the time that the native valve is being cut away.

The cross section of the passage through this catheter may be large enough to allow the blood to flow through this passage, thus limiting or avoiding having to place the patient on extra corporal circulation. The catheter may also have a smaller diameter, making it easier for the device to be introduced into and slid along the bodily vessel, but it then becomes necessary to provide peripheral circulation through an external assistance system such as an extra corporal circulation system.

The catheter comprises a lateral distal opening to allow the blood to reach the bodily vessel, for example the ascending aorta, this opening being formed in such a way that the length of catheter through which the blood flows is as short as possible.

As a preference, the device comprises a distal inflatable balloon, placed at the exterior face of said elongate element; this balloon is shaped to be able to occupy a furled position in which it has a cross section such that it does not impede the sliding introduction of the device into said bodily vessel, and an unfurled position in which it occupies all of the space between the exterior face of said elongate element and the wall of said bodily vessel and, via a peripheral edge that it comprises, bears against this wall.

The balloon is inflated after the series of blades have been positioned one on each side of the native valve, so as to prevent blood reflux during the ablation of the native valve. When said elongate element is a catheter, this balloon also allows this blood to be made to flow only through the catheter.

Once the prosthetic valve has been put in place, the balloon is returned to its furled position so as to re-establish the flow of blood through the bodily vessel.

As a preference, the device comprises a distal filter made of flexible material placed at the exterior face of said elongate element; this filter is shaped to be able to occupy a furled position in which it has a cross section such that it does not impede the introduction and sliding of the device into and in said bodily vessel, and an unfurled position in which it occupies all of the space between the exterior face of said elongate element and the wall of this vessel and, via a peripheral edge that it comprises, bears against this wall.

This filter makes it possible to collect any fragments that may have been generated by the cutting-away of the valve, and to retain them so that they can be removed from the blood circulation.

The device may comprise means for moving said series of blades in the axial direction independently of said balloon and/or of said filter. Once deployed, this or these do not need to be shifted axially in the bodily vessel during the aforementioned axial moving of the series of blades.

Said balloon and/or said filter may also be separate from the device, being mounted on an elongate support element specific to them.

In the event of operations on a mitral valve, this balloon and/or this filter are introduced into the aorta via a peripheral arterial route, and the device for its part is introduced into the heart through the peripheral venous system, as far as the right atrium then into the left atrium through the interatrial septum as far as the mitral valve.

The prosthetic valve may advantageously comprise an armature made of a shape memory material, particularly a nickel-titanium alloy known by the name of "NITINOL".

This same valve may comprise valve leaflets made of biological material (preserved animal or human valve leaflets) or valve leaflets made of a synthetic material such as a polymer.

For a good understanding thereof, the invention is described once again hereinbelow with reference to the appended schematic drawing which, by way of non-limiting example, illustrates a preferred embodiment of the device to which it relates.

FIG. 1 is a view of it in longitudinal section, according to a first embodiment intended to treat a valve in the aorta;

FIG. 2 is a view of it in cross section on II—II of FIG. 1;

FIG. 3 is a view similar to FIG. 2, in another position of the subassembly which it comprises;

FIGS. 5 to 9 are views of it while it is positioned in a heart, at the valve that is to be treated, during the various successive operations by means of which this valve is cut out and the prosthetic valve shown in FIG. 4 fitted;

FIGS. 1 to 3 represent a device 1 for replacing a heart valve by a percutaneous route.

Figure 9:
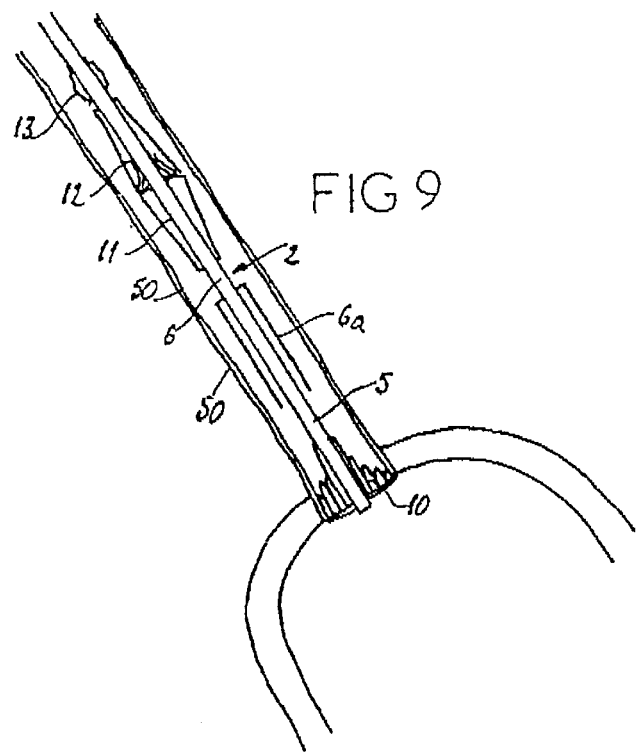

This device comprises a tubular catheter 2 formed from three tubes 5, 6, 7 engaged one inside the other and on which there are placed, from the proximal end to the distal end (considered with respect to the flow of blood, that is to say from right to left in FIG. 1), a prosthetic valve 10, two series of blades 11, 12, a balloon 13 and a filter 14.

The three tubes 5, 6, 7 are mounted so that they can slide one inside the other. The interior tube 5 delimits a passage 15, the cross section of which is large enough to allow blood to flow through it.

At the proximal end, the intermediate tube 6 forms a bell housing 6a delimiting, with the interior tube 5, an annular cavity 17 in which the prosthetic valve 10 is contained in the furled condition.

Figure 4:
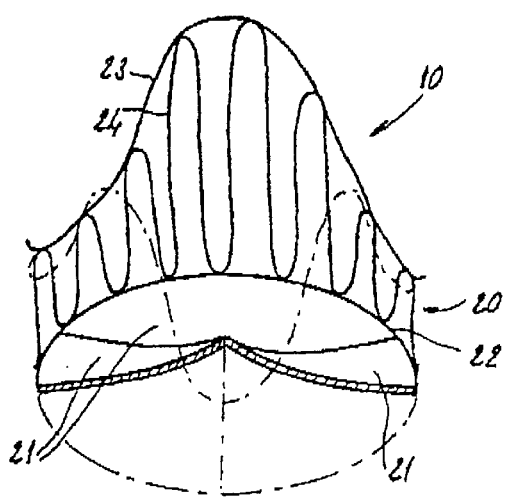
FIG. 4 is a perspective view of a prosthetic valve which can be fitted using it.

FIG. 4 shows that this valve 10 comprises an armature 20 and valve leaflets 21 mounted so that they are functionally mobile on this armature 20.

The armature consists of a collection of wires 22, 23, 24 made of shape memory material, particularly of nickel-titanium alloy known by the name of "NITINOL", namely:

a proximal end wire 22 which, when the valve 10 is in the deployed state, has a roughly circular shape;

a distal end wire 23 forming three corrugations in the axial direction, these corrugations being distributed uniformly around the circumference of the valve 10, and an intermediate wire 24 forming longitudinal corrugations between the wires 22 and 23, this wire 24 being connected to the latter ones via the ends of each of these corrugations.

The valve leaflets 21 for their part are made of biological material (preserved human or animal valve leaflets) or of synthetic material, such as a polymer.

The armature 20 may, when its material is cooled, be radially contracted so that the valve 10 can enter the cavity 17. When this material is heated to body temperature, this armature 20 returns to its original shape, depicted in FIG. 4, in which it has a diameter matched to that of a bodily vessel, particularly the aorta, in which the native valve that is to be treated lies. This diameter of the armature 20 is such that the valve 10 bears against the wall of the bodily vessel and is immobilized in the axial direction with respect to that vessel.

Each series of blades 11, 12 comprises metal elongate blades 30 and an inflatable balloon 31 situated between the catheter 2 and these blades 30.

The blades 30 have a curved profile and are arranged on the circumference of the catheter 2.

The blades 30 of the proximal series 11 are connected pivotably to the tube 6 by their proximal ends and comprise a cutting distal edge 30a, while the blades 30 of the distal series 12 are connected pivotably to the exterior tube 7 by their distal ends and comprise a cutting proximal edge 30b.

The connection between the blades 30 and the respective tubes 6 and 7 is achieved by welding the ends of the blades 30 together to form a ring, this ring being fixed axially to the corresponding tube 6, 7 by crimping this ring onto this tube 6, 7, the pivoting of the blades 30 being achieved by simple elastic deformation of these blades 30.

This pivoting can take place between a position in which the blades 30 are furled, radially internally with respect to the catheter 2 and shown in FIGS. 1 and 2, and a position in which these blades 30 are unfurled, radially externally with respect to this catheter 2 and shown in FIG. 3. In the furled position, the blades 30 lie close to the wall of the tube 6 and partially overlap each other so that they do not impede the introduction and the sliding of the device 1 into and in the bodily vessel in which the native valve that is to be treated lies; in said unfurled position, the blades 30 are deployed in a corolla so that their cutting edges 30a, 30b are placed in the continuation of one another and thus constitute a circular cutting edge visible in FIG. 3.

Each balloon 31, placed between the tube 3 and the blades 30, may be inflated from the end of the catheter 2 which emerges from the patient, via a passage 32 formed in the tube 6. It thus, when inflated, allows the blades 30 to be brought from their furled position into their unfurled position, and performs the reverse effect when deflated.

The axial sliding of the tube 6 with respect to the tube 7 allows the series of blades 11, 12 to be moved axially toward one another, between a spaced-apart position shown in FIG. 1, and a close-together position. In the former of these positions, one series of blades 11 may be placed axially on one side of the native valve while the other series of blades 12 is placed axially on the other side of this valve, whereas in the latter of these positions, the circular cutting edges of these two series of blades 11, 12 are brought into mutual contact and thus cut through the native valve in such a way as to detach it from said bodily vessel.

The tubes 5 to 7 further comprise marks (not visible in the figures) in barium sulfate allowing the axial position of the device 1 with respect to the native valve to be identified percutaneously so that each of the two series of blades 11, 12 can be placed on one axial side of this valve.

These tubes 5 to 7 also comprise lateral distal openings (not depicted) to allow the blood to reach the bodily vessel, these openings being formed in such a way that the length of catheter 2 through which the blood flows is as short as possible, that is to say immediately after the filter 14, in the distal direction.

The balloon 13 is placed on the exterior face of the tube 7, distally with respect to the series 12. This balloon 13 has an annular shape and is shaped to be able to occupy a furled position in which it has a cross section such that it does not impede the introduction and sliding of the device 1 into and in said bodily vessel, and an unfurled position, in which it occupies all of the space between the exterior face of the tube 7 and the wall of said bodily vessel and, via a peripheral edge 13a which it comprises, bears against this wall.

The filter 14 is placed distally with respect to the balloon 13, on the tube 7, to which it is axially fixed. This filter 14 is made of flexible material, for example polyester netting, and is shaped to be able to occupy a furled position in which it has a cross section such that it does not impede the introduction and sliding of the device 1 into and in said bodily vessel, and an unfurled position in which it occupies all of the space between the exterior face of the catheter 2 and the wall of this vessel and, via a peripheral edge 14a which it comprises, bears against this wall.

An inflatable balloon 35 is placed between the tube 7 and the filter 14 so as, depending on whether it is inflated or deflated, to bring the filter 14 into its respective unfurled and furled positions.

In practice, as shown by FIGS. 5 to 9, the device 1 is introduced into said bodily vessel 50 by a percutaneous route and is slid along inside this vessel 50 until each of the series 11, 12 of blades is placed on one side of the native valve 55 that is to be treated (FIG. 5). This position is identified using the aforementioned marks.

When the device is in this position, the proximal part of the catheter 2 is situated in the heart, preferably in the left ventricle, while the aforementioned distal lateral openings are placed in a peripheral arterial vessel, preferably in the ascending aorta.

The balloons 13 and 35 are inflated in such a way as to cause blood to flow only through the passage 15 and prevent blood reflux during the ablation of the valve 55. A peripheral perfusion system is set in place to facilitate this flow.

The blades 30 of the two series 11, 12 are then deployed (FIG. 6) by inflating the balloons 31, then these two series 11, 12 are moved closer together by sliding the tube 6 with respect to the tube 7, until the valve 55 is cut through (FIG. 7).

The blades 30 are then returned to their furled position by deflating the balloons 31 while at the same time remaining in their close-together position, which allows the cut-out valve 55 to be held between them.

The device 1 is then slid axially in the distal direction so as to bring the bell housing 6a to the appropriate position in the vessel 50 (FIG. 8), after which the valve 10 is deployed by sliding the tube 6 with respect to the tube 5 (FIG. 9).

Figure 10:
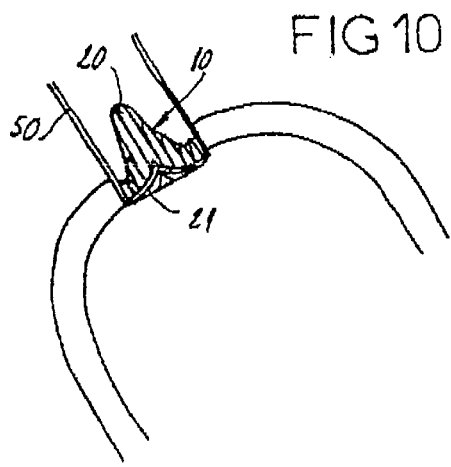
FIG. 10 is a view of the prosthetic valve shown in FIG. 4, after fitting.

The balloons 13 and 35 are deflated then the device 1 is withdrawn and the cut-out valve 55 is recovered (FIG. 10).

Figure 11:
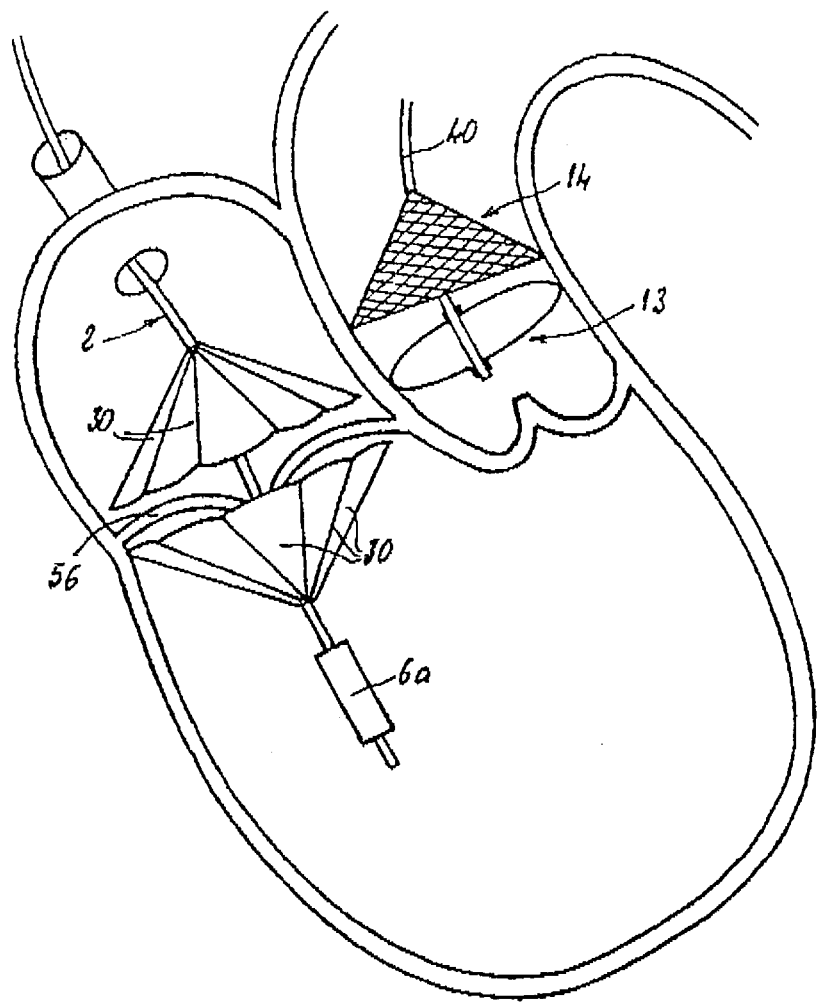
FIG. 11 is a view of the device according to another embodiment, intended for treating a mitral valve.

FIG. 11 shows a second embodiment of the device 1, allowing operation on a mitral valve 56.

The same reference numerals are used to denote the same elements or parts as the aforementioned, as long as these elements or parts are identical or similar in both embodiments.

In this case, the tubular catheter is replaced by a support wire 2, on which one of the series of blades is mounted and by a tube engaged over and able to slide along this wire, on which tube the other series of blades is mounted; the passages for inflating the balloons 31 run along this support wire and this tube; the balloon 13 and the filter 14 are separate from the device 1 and are introduced into the aorta via a peripheral arterial route, by means of a support wire 40 along which the passages for inflating the balloons 13 and 35 run. The device 1, devoid of balloon 13 and the filter 14, is for its part introduced into the heart through the peripheral venous system, as far as the right atrium then into the left atrium through the inter-auricular septum, as far as the valve 56.

For the remainder, the device 1 operates in the same way as was mentioned earlier.

The invention thus provides a device for replacing a heart valve by a percutaneous route, making it possible to overcome the drawbacks of the prior techniques. Indeed the device 1 is entirely satisfactory as regards the cutting-away of the valve 55, 56, making it possible to operate without stopping the heart and making it possible, by virtue of the filter 14, to prevent any dispersion of valve fragments 55, 56 into the circulatory system.

Figure 12:
FIG. 12 is a detailed view of an elongate blade.

It goes without saying that the invention is not restricted to the embodiment described hereinabove by way of example but that, on the contrary, it encompasses all alternative forms of embodiment thereof. Thus, the device may comprise a fourth tube, engaged on and able to slide along the tube 7, this fourth tube comprising the balloon and the filter mounted on it and allowing said series of blades to be moved in the axial direction independently of said balloon and/or of said filter; the blades may be straight as depicted in the drawing or may be curved toward the axis of the device at their end which has the cutting edge, so as to eliminate any risk of lesion in the wall of the bodily vessel, as shown in FIG. 12; the filter 14 may be of the self-expanding type and normally kept in the contracted position by a sliding tube, which covers it, making the balloon 35 unnecessary.

What is claimed is:

1. A device (1) for replacing, via a percutaneous route, a heart valve (55, 56) located in a bodily vessel (50), characterized in that it comprises:

an elongate support element (2);

a first series (11) of elongate blades (30) arranged around the circumference of said elongate element (2); these blades (30) are pivotably connected to said elongate element (2) at their proximal longitudinal end and each have a cutting edge (30*a*) at their distal longitudinal end; said blades (30) capable of pivoting with respect to said elongate element (2) between a furled position in which they are near to the wall of the elongate element (2) so that they do not impede the introduction and sliding of the device (1) into and in the bodily vessel (50) in which a valve (55, 56) is located, particularly within the aorta, and an unfurled position in which these blades (30) are deployed into a corolla in such a way that their cutting edges (30*a*) are placed in the continuation of one another and thus constitute a circular cutting edge;

a second series (12) of blades (30) which is arranged after said first series (11) of blades in the distal direction; the blades (30) of this second series (12) of blades have a structure identical to that of the blades (30) of said first series (11) of blades except that these blades (30) of this second series (12) are connected to said elongate element by their distal longitudinal end and each have a cutting edge (30*b*) at their proximal longitudinal end;

means (31) for bringing the blades (30) of said first and second series (11, 12) of blades from a furled position to an unfurled position;

means (6, 7) for moving said series (11, 12) of blades axially toward one another, between a position in which these series (11, 12) of blades are away from each other and in which one series (11) of blades can be placed axially on one side of the native valve (55, 56) while the other series (12) of blades is placed axially on the other side of this valve (55, 56), and a close-together position in which the circular cutting edges of these two series (11, 12) of blades are brought into mutual contact and thus cut through the native valve (55, 56) so as to detach it from said bodily vessel (50); and means of identifying, by a percutaneous route, the axial position of the device (1) with respect to the native valve (55, 56) so as to position each of the two aforementioned series (11, 12) of blades on one side of this valve.

2. The device (1) as claimed in claim 1, characterized in that it comprises a proximal prosthetic valve (10), with a radially deployable structure, it being possible for this prosthetic valve (10) to occupy a furled position in which it is near the wall of said elongate element (2) and does not impede the introduction and sliding of the device (1) into and in said bodily vessel (50), and an unfurled position in which it bears against the wall of this vessel (50) and is able to replace the native heart valve (55, 56).

3. The device as claimed in claim 1, characterized in that said elongate support element is a tubular catheter (2).

4. The device as claimed in claim 1, characterized in that it comprises a distal inflatable balloon (13), placed at the exterior face of said elongate element (2); this balloon (13) is shaped to be able to occupy a furled position in which it has a cross section such that it does not impede the sliding introduction of the device (1) into said bodily vessel (50), and an unfurled position in which it occupies all of the space between the exterior face of said elongate element (2) and the wall of said bodily vessel (50) and, via a peripheral edge (13*a*) that it comprises, bears against this wall.

5. The device as claimed in claim 1, characterized in that it comprises a distal filter (14) made of flexible material placed at the exterior face of said elongate element (2); this filter (14) is shaped to be able to occupy a furled position in which it has a cross section such that it does not impede the introduction and sliding of the device (1) into and in said bodily vessel (50), and an unfurled position in which it occupies all of the space between the exterior face of said elongate element (2) and the wall of this vessel (50) and, via a peripheral edge (14*a*) that it comprises, bears against this wall.

6. The device as claimed in claim 4, characterized in that it comprises means for moving said series of blades in the axial direction independently of said balloon and/or of said filter.

7. The device as claimed in claim 4, characterized in that said balloon (13) and/or said filter (14) are mounted on an elongate support element specific to them and are separate from the device (1).

8. The device as claimed in claim 2, characterized in that the prosthetic valve (10) comprises an armature (20) made of a shape memory material, particularly a nickel-titanium alloy known by the name of "NITINOL".

9. The device as claimed in claim 2, characterized in that the prosthetic valve (10) comprises valve leaflets (21) made of biological material (preserved animal or human valve leaflets) or valve leaflets made of a synthetic material such as a polymer.

10. The device as claimed in claim 1, characterized in that the blades are curved toward the axis of the device at their end that has the cutting edge.

11. The device as claimed in claim 3, characterized in that the catheter comprises a lateral distal opening to allow the blood to reach the bodily vessel, for example the ascending aorta, this opening being formed in such a way that the length of catheter through which the blood flows is as short as possible, and so as to allow the blood to flow between the heart and a peripheral vessel.

* * * * *